(12) United States Patent
Panek-Finda et al.

(10) Patent No.: US 7,018,612 B1
(45) Date of Patent: Mar. 28, 2006

(54) METHOD OF PREPARING A RADIOACTIVE RHENIUM COMPLEX SOLUTION

(75) Inventors: Helena Panek-Finda, Heiloo (NL); David W. Pipes, Ballwin, MO (US)

(73) Assignee: Mallinckrodt Inc., St. Louis, MO (US)

( * ) Notice: Subject to any disclaimer, the term of this patent is extended or adjusted under 35 U.S.C. 154(b) by 0 days.

(21) Appl. No.: 07/972,474

(22) PCT Filed: Jul. 2, 1991

(86) PCT No.: PCT/US91/04704

§ 371 (c)(1),
(2), (4) Date: Dec. 14, 1992

(30) Foreign Application Priority Data

Jul. 6, 1990 (EP) .......................................... 90201817

(51) Int. Cl.
*A61K 51/04* (2006.01)

(52) U.S. Cl. ........................... 424/1.77; 534/10; 534/14
(58) Field of Classification Search ................ 424/1.1, 424/1.77; 423/2; 534/10, 14
See application file for complete search history.

(56) References Cited

U.S. PATENT DOCUMENTS

| 4,451,450 | A | * | 5/1984 | Subramanyam | ............. | 424/1.1 |
| 4,455,291 | A | * | 6/1984 | Tweedle | ..................... | 424/1.1 |
| 4,935,222 | A | * | 6/1990 | Deutsch et al. | ............. | 424/1.1 |
| 5,192,526 | A | * | 3/1993 | Pipes | ......................... | 424/1.1 |

OTHER PUBLICATIONS

*Concise Encyclopedia Chemistry*, 1994, p. 107.*
Mortimer, *Chemistry, A Conceptual Approach*, 1979, p. 471.*

* cited by examiner

*Primary Examiner*—Gary Geist

(57) ABSTRACT

The invention relates to a method of preparing a solution of a radioactive rhenium complex, by reacting at elevated temperature a radioactive perrhenate in a substantially aqueous solution with a ligand in the presence of a reductant and optionally an antioxidant under substantially anaerobic conditions, wherein said reaction is carried out at a pH from approx. 1.5 to approx. 5 and by heating the reaction components for at least 10 min. at a temperature of at least 100° C. The invention further relates to a kit for performing said method.

15 Claims, No Drawings

METHOD OF PREPARING A RADIOACTIVE RHENIUM COMPLEX SOLUTION

The invention relates to a method of preparing a solution of a radioactive rhenium complex, by reacting at elevated temperature a radioactive perrhenate in a substantially aqueous solution with a ligand in the presence of a reductant and optionally an antioxidant under substantially anaerobic conditions. Such a preparation method has been described by Deutsch et al, viz. in U.S. Pat. No. 4,778,672, in European patent application 250966 and in Nucl. Med. Biol. 13, 1986, 465–477. In particular in their last publication, Deutsch and coworkers have explained in detail the differences between the preparation of rhenium complexes and of technetium complexes and the practical consequences thereof in nuclear medicine applications. Re complexes are more stable in their higher oxidation states than are analogous Tc complexes. Consequently reduced Re radiopharmaceuticals will tend to be re-oxidized back to perrhenate. This instability is a serious disadvantage in the use of Re radiopharmaceuticals because the impurities, formed during preparation and storage of these pharmaceuticals, such as uncomplexed perrhenate and rhenium dioxide, form a serious radiation burden for various organs and tissues, such as kidneys, liver and blood. As a matter of fact, radioactive labelled rhenium compounds are intended for combating or controlling tumors or can be used as palliation agents for the pain caused by certain malignant tumors. It will therefore by evident, that such radiolabelled compounds which are intended, for example, for damaging tumors, are highly injurious to the health of the patient if arrived in a wrong place of the body.

Deutsch et al have recognized the above problems and they have proposed a variety of measures to counter these problems. First, they have proposed to perform the preparation of the desired complex and to store said complex under substantially anaerobic conditions, to add to said complex an antioxidant and to use for the preparation a large excess of reductant, thus requiring a large amount of ligand. Second, they have proposed to purify the complex solution by a chromatographic procedure just prior to use, which they consider as most effective. Such a chromatographic procedure involves rather complicated manipulation of highly radioactive material, such as loading the prepared column with the radioactive solution to be purified, elution and collection of the individual fractions, and selecting and combining of the proper fractions comprising the purified rhenium complex. The purified rhenium complex must be administered to the patient within one hour of preparation to avoid degradation. Therefore this laborious purification method involving the manipulation of highly radioactive material should be performed in the clinic or clinical hospital where the radiopharmaceuticals is to be used.

It is the object of the present invention to provide a method of preparing a solution of a radioactive rhenium complex as defined in the opening paragraph, in which such a laborious purification just prior to use is not necessary. Further, it is the object of the present invention to provide a method of preparing a rhenium-comprising radiopharmaceutical with an improved stability.

This object can be achieved by reacting at elevated temperature a radioactive perrhenate in a substantially aqueous solution with a ligand in the presence of a reductant and optionally an antioxidant under substantially anaerobic conditions, which method is characterized according to the present invention, in that said reaction is carried out at a pH from approx. 1.5 to approx. 5 and by heating the reaction components for at least 10 min. at a temperature of at lest 100° C. Surprisingly it has been found, that under the above reactions conditions a product is obtained which is sufficiently stable to be stored and transported to the user, i.e. the clinic or clinical laboratory, without objectionable deterioration of the radioactive rhenium complex. Consequently a purification of the product prior to use is not necessary. In addition it has been found, that the product obtained in this manner presents a superior biological behaviour in comparison with the product prepared according to the known method.

The preparation of the solution of the radioactive rhenium complex can be carried out conveniently by the producer in a reaction vessel suitable for performing reactions under elevated pressure, for example in an autoclave. Preferably the method of the invention is carried out in such manner, that a radioactive perrhenate in a substantially aqueous solution, having a concentration of rhenium in said solution within the range of approx. $5 \times 10^{-6}$ M to approx. $2 \times 10^{-3}$ M, is reacted with said ligand in the presence of said reductant, by mixing said solution with a solution of a lyophilized solid, comprising an excess of said reductant and of said ligand with respect to the quantity of rhenium, and by then heating said reaction mixture.

Of course the ligand to be used in the above complexing reaction is a ligand that complexes with rhenium. For the intended purpose of the radiopharmaceutical to be prepared a bone seeking ligand is preferred. Suitable bone seeking ligands are polyphosphates, pyrophosphates, phosphonates, diphosphonates, phosphonites and imidodi-phosphates. The therapeutic radiopharmaceuticals are in particular intended for use as palliation agents for the pain caused by metastatic bone cancer. For this purpose are particularly effective rhenium complexes of diphosphonate ligands selected from 1-hydroxyethylidene-1,1-diphosphonic acid, hydroxymethylene diphosphonic acid, methylene diphosphonic acid, (diphosphonomethyl)-butanedionic acid, aminoethane diphosphonic acid, (dimethylamino)methyl diphosphonic acid, ethylenediamine tetra(methylene phosphonic acid) and propane-3-amino-1-hydroxy-1,1-diphosphonic acid, preferably 1-hydroxyethylidene-1,1-diphosphonic acid.

As regards the radiation characteristics, rhenium-186 and rhenium-188 are suitable radionuclides of rhenium for the above therapeutic application.

Also the pH of the solution during the complex formation may vary between certain limits, a pH between approx. 2 and approx. 2.5 is preferred to advance the formation of the desired rhenium complex.

It has been observed, that the best results are obtained when the above complex-forming reaction is carried out by heating the reaction components for at least 10 min. at a temperature of approx. 120° C. Then the rhenium complex obtained proves to have a very high resistance against degradation on ageing and a surprisingly enhanced biological performance, as will be apparent from the Examples.

The present invention also relates to a method of preparing a ready-to-inject product, i.e. a sterile radiopharmaceutical composition comprising a radioactive rhenium complex solution, wherein said solution is prepared as described herein before and then the pH of the product, obtained is adjusted to approx. 5–6 by addition of a suitable buffer solution under an inert atmosphere, if desired while adding a pharmaceutically acceptable dilution liquid, after which the final radiopharmaceutical composition is sterilized by autoclaving at approx. 120° C. and subsequently stored for a period of at least 3 hours, before administration. Remarkably it has been observed, that said radiopharmaceutical composition is not in an optimum condition for administration to humans directly after preparation, but that a time period of at least 3 hours between autoclaving and administration is needed to obtain the desired radioactive rhenium complex in said composition having a high radiochemical purity. So apparently in this time period the desired rhenium complex is recovered. The thus at least 3-hour-aged radiopharmaceutical composition can be stored and transported to the user at ambient temperature without noticeable deterioration and can there be directly administered to a patient without any manipulations.

Alternatively said sterile radiopharmaceutical composition can be prepared by first preparing aid radioactive rhenium complex as described hereinbefore and by then autoclaving the product obtained at approx. 120° C., after which the pH of the sterile product is adjusted to 4–9, preferably to 5–8, by addition of a suitable buffer solution under an inert atmosphere, if desired while adding a pharmaceutically acceptable dilution liquid. The composition thus obtained is immediately ready for use, i.e. for administration to a patient. The addition of the buffer solution should preferably be performed prior to administration, so preferably in the clinic or hospital. Because the operation of adding a buffer solution to the radioactive material is a so simple procedure, this method is not disadvantageous compared to the former method of preparing the radiopharmaceutical composition. Suitable buffers are pharmaceutically acceptable buffers, such as acetate buffer, citrate buffer, phosphate buffer. TRIS buffer and HEPES buffer. If the method of preparing the radioactive rhenium complex solution is performed by heating the reaction components at a temperature of approx. 120 20 C., which reaction temperature is preferred, the complexing reaction and the autoclaving can even by combined. In other words, in that case a separate autoclaving can be omitted.

Further the invention relates to the ready-for-use product, i.e. the sterile radiopharmaceutical composition comprising the product prepared according to the method as described above, and to the use of said composition for radiotherapeutically treating a warm-blooded living being. For this purpose said composition is administered to said being in a quantity effective for combating or controlling tumors or for palliating the pain caused by certain metastatic tumors.

Finally the invention relates to a kit for preparing a sterile radiopharmaceutical composition according to the above alternative preparation method. As stated before, in performing said alternative methodthe pH of the final autoclaved product should be adjusted by adding a buffer solution, preferably prior to administration. Consequently, such a kit for preparing a sterile radiopharmaceutical composition for therapeutical application comprises (i) a sterile radioactive rhenium complex solution obtained as described above, and (ii) a buffer solution suitable for adjusting the pH of the solution defined sub (i) to 4–9, preferably to 5–8, to which solution, if desired, a pharmaceutically acceptable dilution liquid has been added.

The invention will now be described in more detail with reference to the following specific examples.

EXAMPLE I

Preparation of rhenium-186 labelled 1-hydroxyethylidene diphosphonate (Re186-HEDP bulk)

Re186-radioisotope is obtained by irradiation of Re185-metal (97.4% enriched) at high flux of thermal neutrons in the nuclear reactor. The irradiated target material is processed to the final chemical form of $NaReO_4$ which is to be used as a starting radioactive material for preparation of Re186-HEDP complex.

The sodium perrhenate of a high chemical purity is obtained by oxidation of Re-metal with 30%-hydrogen peroxide followed by complete evaporation to dryness. The dry residue—free of hydrogen perioxide—is then dissolved in 0.9% sodium chloride aqueous solution and the radioactive built containing the Re186-radioisotope in the form of sodium perrhenate is finally formulated to the solution, where the rhenium concentration lies between 10–200 ug/ml and the radioactive concentration is equal to expected precalibrated activity at the time of administration. Natural pH of this solution lies between 5 and 5.5. This way processed sodium perrhenate does not contain any intermediate products and contaminants. Sterility, apyrogenicity and absence of particulate matter is secured by bacterial filtration through Milex Gs® filter.

HEDP-reaction mixture—is prepared by lyophilizing deaerated concentrated aqueous bulk solution of disodium 1-hydroxymethylidene-1,1-diphosphonate, gentisic acid (antioxidant) and tin(II)chloride dihydrate (reductant) in concentrations of 100, 30 and 35 mg per 1.5 ml respectively. The volume of the solution to be lyophilized is dependent on the size of the batch to be prepared. An amount of 0.15 ml of the bulk solution to be lyophilized is equal to one patient dosis.

Re186-HEDP bulk—is prepared by addition of equal volume (1 ml $Na(Re186)O_4$/one patient dosis) of the sterile Re186-built solution to the contents of the vial containing the HEDP-reaction mixture, avoiding contamination of the vial interior with air. After reconstitution of the lyophilized HEDP-reaction mixture in $Na(Re186)O_4$ solution under inert gas atmosphere, e.g. nitrogen, the radioactive solution is autoclaved for 10–30 minutes at 121° C.

The pH of the solution in the reaction vial is typically between 2–2.5. This solution typically contains more than 99% of the Re186-HEDP complex.

EXAMPLE II

Preparation of a sterile radiopharmaceutical composition comprising Re186-HEDP

Re186-HEDP-Injection pH 5 . 5.5—is prepared by mixing of the Re186-HEDP bulk, obtained according to Example I, with equal volume of deaerated sodium acetate buffer solution pH 7.5–9.5 under inert atmosphere. 2-ml portions of the pH-adjusted Re186-HEDP bulk are dispensed in the autoclavable transport vials which are than crimp-sealed under inert gas atmosphere and autoclaved. Typical pH of this solution if 5–5.5 and content of released $186ReO_4^-$ due to the autoclaving of Re186-HEDP complex at pH>5 might be as high as 7–8%. this solution is not in an optimum condition for administration to humans directly after preparation, but, a time period of at least 3 hours between autoclaving and administration is needed for recovery of the Re186-HEDP complex to approx. 99%. This way prepared radiopharmaceutical 3-hours-aged might be directly administered to a patient without further adjustments of pH or concentration.

EXAMPLE III

Preparation of a sterile radiopharmaceutical composition comprising Re186-HEDP

Re186-Injection pH 2.2–2.5 is prepared by dispensing of 1 ml of Re186-HEDP bulk under an inert atmosphere and autoclaving of the crimp-sealed vials. This acidic solution can be used at any time after autoclaving, when properly adjusted by addition of 1 ml acetate buffer prior administration to the patient. The radiochemical purity of Re186-HEDP in this solution is typically ≧99%.

EXAMPLE IV

Comparative experiments in recovery of Re186-HEDP after autoclaving at adjusted pH under anaerobic and aerobic conditions A bulk solution of Re186-HEDP prepared under anaerobic conditions and adjusted to pH 5.3 with acetate buffer is dispensed into vials under nitrogen and normal air atmosphere respectively. The vials contain approx. 400–600 MBq Re186. Both groups of test vials are autoclaved and submitted to consecutive radiochemical purity analysis at the time intervals from $T_{0h}$–$T_{24h}$. The results are compared with radiochemical purity of the Re186-HEDP bulk prior to autoclaving. Results in Table A demonstrate the instability of the Re186-HEDP complex under aerobic conditions and also recovery of the Re186-HEDP to original radiochemical purity in time of storage under anaerobic condition. It can be observed, that heating of Re186-HEDP complex at pH which is unfavorable to the Re186-HEDP complex formation releases always some free $186ReO_4^-$. On the other hand, when the heating and storage of the complex is performed in absence of oxygen, the Re186-HEDP rather quickly recovers to the original state.

TABLE A

| Re186-HEDP-Bulk-$N_2$: | | | |
| --- | --- | --- | --- |
| | $T_{0h}$ % | $T_{6h}$ % | $T_{24h}$ % |
| Re-HEDP | 99.66 | 99.53 | 99.67 |
| $ReO_4^-$ | 0.28 | 0.41 | 0.28 |
| $ReO_2$ | 0.06 | 0.06 | 0.05 |

| Re186-HEDP-Autoclaved —$N_2$ (pH 5.3): | | | | |
| --- | --- | --- | --- | --- |
| | $T_{0h}$ % | $T_{3.5h}$ % | $T_{5.75h}$ % | $T_{24h}$ % |
| Re-HEDP | 93.75 | 98.55 | 99.56 | 99.92 |
| $ReO_4^-$ | 6.22 | 1.4 | 0.36 | not detectable |
| $ReO_2$ | 0.03 | 0.05 | 0.08 | 0.08 |

| Re186-HEDP-Autoclaved-Air: | | | | |
| --- | --- | --- | --- | --- |
| | $T_{0h}$ % | $T_{3.5h}$ % | $T_{5.75h}$ % | $T_{24h}$ % |
| Re-HEDP | 70.63 | 58.9 | 61.48 | 53.42 |
| $ReO_4^-$ | 29.35 | 41.06 | 38.31 | 46.56 |
| $ReO_2$ | 0.02 | 0.04 | 0.01 | 0.02 |

Note: Re means Re186

The influence of the reaction temperature on the stability of Re186-HEDP is demonstrated in a comparative experiment, where the labelling of HEDP with rhenium-186 is carried out as describe din Example I, but now by heating for 15 minutes in a boiling water bath, i.e. at a temperature just below 100° C. It is observed that the product thus obtained gradually degrades during storage at ambient temperature, viz. from 99.12% at t=0 down to 93.72% at t=24 h.

EXAMPLE V

When using the preparation methods as described in Examples I, II and III, the injectable composition a–f are obtained as follows:

composition a;
  a. dissolution of $186ReO_4^-$ residue (isotope production) in reaction solution under an inert atmosphere.
  b. heating the reaction mixture at temperature >100° C. under inert atmosphere >10 min.
  c. pH adjustment (acetate buffer) and dilution to appropriate volume
  d. dispensing of the Re186-HEDP pH >5 into the vials
  e. autoclaving of the vials under an inert atmosphere
composition b;
  a dissolution of $186ReO_4^-$ residue in reaction solution under an inert atmosphere
  b. adjustment of the volumic activity with the reaction solution
  c. dispensing of the reaction mixture (1 ml/vial) under an inert atmosphere
  d. autoclaving of the dispensed reaction mixture
  e. addition of 1 ml acetate buffer prior to administration
composition c;
  a. dissolution of lyophilized reaction mixture in $Na(re186)O_4^-$ solution under an inert atmosphere
  b. heating of the Re186-reaction mixture for 10 or more minutes at temperature >100° C.
  c. adjustment of pH to 5–5.5 by addition of acetate buffer under inert atmosphere
  d. dispensing of the Re186-HEDP pH 5 . 5.5 (2 ml/vial) under an inert atmosphere
  e. autoclaving of the vials
composition d:
  a. dissolution of the lyophilized reaction mixture in $Na(Re186)O_4$ under an inert atmosphere
  b. dispensing of the Re186-reaction mixture under an inert atmosphere (1 ml/vial)
  c. autoclaving of the dispensed Re186-reaction mixture
  d. addition of acetate buffer (1 ml) to the Re186-HEDP prior to administration
composition e;
  a. dispensing of calibrated $Na(Re186)O_4$ into the vials containing a freeze-dried 1-patient dose of the reaction mixture—under an inert atmosphere
  b. autoclaving of the vials
  c. addition of 1 ml citrate buffer prior to administration in the hospital
composition f;
  a. dispensing of calibrated $Na(Re186)O_4$ into the vials containing a' freeze-dried 1-patient dose of the reaction mixture—under an inert atmosphere
  b. autoclaving of the vials
  c. addition of 1 ml acetate buffer to each vial under an inert atmosphere
  d. autoclaving of the Re186-HEDP—pH 5–5.5

Composition b, d and e can be delivered as two-component (vial) kits, a first vial containing a solution of the radioactive rhenium complex, and a second vial containing a buffer solution for adjusting the pH of the radiopharmaceutical prior to administration.

EXAMPLE VI

Comparative biological experiment

Composition g and h are prepared identically, viz. by addition of 1 ml $186ReO_4^-$ to the lyophilized HEDP reaction mixture under anaerobic conditions and heating the reconstituted mixture in a boiling water bath for 15 minutes. After brief cooling, 1 ml of acetate buffer is added to each preparation respectively under nitrogen. Composition g is administered to the test animals within 0.5 hour after addition of acetate buffer, while composition h is administered after 24 hours of storage at room temperature.

Composition k and l are prepared batchwise, by addition of 5 ml 186ReO$_4^-$ to lyophilized reaction mixtures in fivefold quantities and autoclaving for 25 minutes at 121° C. 1-ml portions of composition k are dispensed into the vials, crimp-sealed and set aside for 24 hours storage at room temperature, to be adjusted with 1 ml of the acetate buffer prior to administration. On the other hand, 1-ml portions of composition l are immediately after dispensing adjusted by addition of 1 ml acetate buffer and autoclaved again (25 min. at 121° C.), to be set aside at room temperature and administered 24 hours after preparation.

All operations are performed under anaerobic conditions.

4 Groups of Sprague-Dawley female rats are injected with the above Re186-HEDP composition g, h, k and l in order to compare the biological performance of these compositions.

Three hours after injection the test animals are sacrificed and the organ distribution is determined. From this organ distribution the bone/organ ratio is determined. The values in table B below are the average values of four test animals per group.

TABLE B

| composition | bone/organ ratio | | |
|---|---|---|---|
| | bone/blood | bone/kidney | bone/muscle |
| g | 17.469 | 1.937 | 208.847 |
| h | 20.464 | 2.097 | 234.336 |
| k | 27.594 | 3.184 | 302.360 |
| l | 27.766 | 3.373 | 338.217 |

The above results show, that the biological performance of the Re186-HEDP complex prepared by autoclaving at approx. 120° C. is appreciably enhanced in comparison with the complex, prepared by heating in a boiling water bath.

What is claimed is:

1. A method for preparing a sterile radiopharmaceutical composition comprising:
    preparing a solution of a radioactive rhenium complex;
    sterilizing the solution by autoclaving the solution for a period of time sufficient to render the solution sterile; and
    adjusting the pH of the sterile solution to a range of about 4 to about 9 by addition of a sterile buffer solution under an inert atmosphere.

2. The method of claim 1 wherein the pH of the sterile solution is adjusted to a range of about 5 to about 8.

3. The method of claim 1 wherein the radioactive rhenium complex solution comprises radioactive rhenium bound to a bone seeking ligand.

4. The method of claim 3 wherein the bone seeking ligand is a polyphosphate, pyrophosphate, phosphonate, diphosphonate, phosphonite or imidodiphosphate.

5. The method of claim 4 wherein the bone seeking ligand is a diphosphonate.

6. The method of claim 5 wherein the bone seeking ligand is selected from the group consisting of 1-hydroxy ethylidene-1,1-diphosphonic acid, hydroxymethylene diphosphonic acid, methylene diphosphonic acid, (diphosphonomethyl)-butanedionic acid, aminoethane diphosphonic acid, (dimethylamino)methyl diphosphonic acid, ethylenediamine tetra(methyle phosphonic acid), and propane-3-amino-1-hydroxy-1,1-diphosphonic acid.

7. The method of claim 6 wherein the bone seeking ligand is 1-hydroxy ethylidene-1, 1-diphosphonic acid.

8. The method of claim 3 wherein the radioactive rhenium is rhenium-186 or rhenium-188.

9. A method of preparing a sterile radiopharmaceutical composition comprising the steps of:
    preparing a radioactive rhenium complex solution;
    adjusting the pH of the solution to a range of about 5 to about 6;
    sterilizing the pH adjusted solution by autoclaving for a period of time sufficient to render the solution sterile; and
    storing the sterilized solution for a period of about 3 hours before administration of the solution.

10. The method of claim 9, wherein the radioactive rhenium complex solution comprises radioactive rhenium bound to a bone seeking ligand.

11. The method of claim 10 wherein the bone seeking ligand is a polyphosphate, pyrophosphate, phosphonate, diphosphonate, phosphonite or imidodiphosphate.

12. The method of claim 11 wherein the bone seeking ligand is a diphosphonate.

13. The method of claim 12 wherein the bone seeking ligand is selected from the group consisting of 1-hydroxy ethylidene-1,1-diphosphonic acid, hydroxymethylene diphosphonic acid, methylene diphosphonic acid, (diphosphonomethyl)-butanedionic acid aminoethane diphosphonic acid, (dimethylamino)methyl diphosphonic acid, ethylenediamine tetra(methylene phosphonic acid), and propane-3-amino-1-hydroxy-1,1-diphosphonic acid.

14. The method of claim 13 wherein the bone seeking ligand is 1-hydroxy ethylidene-1, 1-diphosphonic acid.

15. The method of claim 10 wherein the radioactive rhenium is rhenium-186 or rhenium-188.

* * * * *